United States Patent [19]

Hoegnelid et al.

[11] Patent Number: 5,514,171
[45] Date of Patent: May 7, 1996

[54] PRESSURE AND HEART MOVEMENT SENSOR FOR HEART STIMULATORS

[75] Inventors: Kurt Hoegnelid, Vaesterhaninge; Kenth-Ake-Sune Nilsson, Akersberga; Nils Holmstroem, Jaerfaella, all of Sweden; Roland Heinze, Berlin, Germany; Karin Ljungstroem; Pierre Westin, both of Stockholm, Sweden

[73] Assignee: Siemens Elema AB, Solna, Sweden

[21] Appl. No.: 271,522

[22] Filed: Jul. 7, 1994

[30] Foreign Application Priority Data

Jul. 7, 1993 [SE] Sweden .................................. 9302357

[51] Int. Cl.⁶ ........................................................ A61N 1/05
[52] U.S. Cl. ........................................... 607/122; 128/675
[58] Field of Search ..................................... 128/672, 673, 128/675; 607/19, 20, 23, 119, 122

[56] References Cited

U.S. PATENT DOCUMENTS

| 4,140,132 | 2/1979  | Dahl .                       |
|-----------|---------|------------------------------|
| 4,566,456 | 1/1986  | Koning et al. .              |
| 4,784,151 | 11/1988 | Frank et al. .               |
| 4,791,931 | 12/1988 | Slate .                      |
| 4,924,872 | 5/1990  | Frank .                      |
| 5,129,394 | 7/1992  | Mehra .                      |
| 5,353,800 | 10/1994 | Pohndorf et al. ..... 128/675 |

FOREIGN PATENT DOCUMENTS 3223987  1/1983  Germany .

Primary Examiner—William E. Kamm
Assistant Examiner—Scott M. Getzow
Attorney, Agent, or Firm—Hill, Steadman & Simpson

[57] ABSTRACT

A pressure and heart movement sensor for a heart stimulator, includes an electrode system for implantation with an electrode cable containing at least two electrical conductors leading to electrode poles. A measurement device is arranged to measure an electrical quantity between the electrical conductors, which quantity varying according to the pressure applied to the electrode cable. Alternately, the electrode cable contains at least one electrical conductor, and the measurement device is arranged to measure the impedance between the conductor and ambient medium and to deliver an output signal, which varies according to the impedance measured, when the electrode cable is subjected to pressure.

30 Claims, 3 Drawing Sheets

PRESSURE AND HEART MOVEMENT SENSOR FOR HEART STIMULATORS

BACKGROUND OF THE INVENTION

1. Field of the Invention

The present invention relates to a pressure and heart movement sensor for a heart stimulator, including an electrode system for implantation with an electrode cable containing at least one conductor leading to one electrode pole, or alternately at least two conductors leading to electrode poles.

2. Description of the Prior Art

For arrhythmia treating implants, such as heart stimulators, pressure sensors for controlling the stimulator are ideal sensors in many respects. With a pressure sensor, hemodynamics can be measured in the cases of both tachyarrhythmias and bradyarrhythmias. Heart contractions can be sensed and used for autocapture and atrial synchronization. Furthermore, the time derivative dP/dt is a good rate-response parameter.

For these types of applications, known pressure sensors normally contain a piezoelectric or piezoresistive pressure element. A pacemaker controlled with this type of sensor is previously known from, e.g., U.S. Pat. No. 4,140,132. One disadvantage of this type of sensor is that the sensor requires additional electrical lines, normally two. The electrode cable must therefore contain relatively many conductors. Another disadvantage of this design is that special impedance demands must often be made on the pressure element in order, e.g., to eliminate the problem of leakage resistances, making it necessary to place electric components out near the sensor itself. Another disadvantage is the fact that the piezoelectric ceramic material itself is hard and brittle.

Capacitive accelerometers are also previously known, cf. German OS 3 223 987, in which an inertial mass forms one of the capacitor plates so the capacitance changes when the plate is subjected to acceleration. This technique cannot be used for implantable pressure and heart movement sensors of the type discussed above. Such a sensor would also require additional conductors.

The existence of a capacitive coupling between electrical conductors and between a conductor and ambient medium is well-known, as described by Tietze and Schenk, Halbleiter-Schaltungstechnik, Springer-Verlag, Berlin Heidelberg New York 1978, 4th edition, page 647. The magnitude of the capacitive coupling depends inter alia on the dielectric constant of the materials between the conductors and the distance between them.

Such a capacitive coupling is naturally present even between the conductors in a bipolar pacemaker electrode system and between the conductors and ambient electrolyte, i.e. blood. A capacitance of about 100 pF has been measured between the two conductors in a bipolar pacemaker electrode system in dry conditions. The two conductors here must of course not terminate in electrical poles in direct contact with one another via the electrolyte or body fluid, since this would result in short-circuiting of the capacitance. The resistance between the conductors must be sufficiently large.

SUMMARY OF THE INVENTION

The shape of a bipolar electrode system implanted in a patient changes when the patient moves, thereby changing the capacitance between electrode conductors and between the conductors and ambient electrolyte. The patient's heart movements can therefore be expressed as changes in capacitance.

If a medium, whose resistivity or piezoelectric voltage changes when the conductors are moved or deformed by the pressure of blood or heart movements, is arranged between the conductors in a bipolar electrode system, changes in pressure and heart movements will appear as changes in resistance or voltage between the conductors.

An object of the present invention is to achieve, by utilization of these effects, a new type of pressure and heart movement sensor in which the above-described disadvantages of previously known sensors for controlling heart stimulators are eliminated.

The above object is achieved in accordance with the principles of the present invention in an implantable heart stimulator, having an electrode system including an electrode cable containing at least two electrical conductors leading to electrode poles, with a measurement device arranged to measure an electric quantity between the electrical conductors, the measured quantity varying according to the pressure which is applied to the electrode cable.

Thus, the pressure and heart movement sensor according to the invention is based on the circumstance that pressure in the heart increases every time the heart beats, this increasing pressure compressing the electrode system so the medium between the conductors of the electrode system is compressed with attendant changes in the medium's electrical properties. Furthermore, the electrode and its conductor move every time the heart beats. These changes in shape or deformations of the electrode system cause changes in the distance between the electrode conductors in, e.g., a bipolar electrode system, or between an electrode conductor and ambient electrolyte. This change in distance, as well as the above mentioned changes in the electrical properties of the intermediate medium, result in a change of the impedance between electrode conductors and ambient electrolyte or in a change in impedance or piezoelectric voltage between two electrode conductors, which electrical quantities can be measured. In this very simple manner, the patient's heart movements and pressure changes can be detected with the ordinary heart stimulator electrode.

According to one advantageous embodiment, the sensor medium is arranged to form at least a part of one of the conductors, and the measurement device is connected to two points on this conductor, on either side of an area of the sensor medium, in order to measure changes in an electrical quantity in this area when the sensor medium is subjected to pressure. This is an advantageous, practical realization of the invention.

According to another advantageous embodiment of the sensor according to the invention, the sensor medium is an insulating, elastic substance, such as silicone rubber, containing granules of conductive material, such as granules of carbon. When the sensor medium is subjected to pressure, the resistance between the conductors changes because of changes in intergranular contacts. When the conductors are compressed more contacts are formed between the carbon granules and the resistance drops.

In a further embodiment of the sensor according to the invention, the silicone rubber filling in the preceding embodiment is replaced with a carbon fiber mat, a conductive polymer or a sodium chloride solution, thereby improving conductivity.

In other advantageous embodiments of the sensor according to the invention, the sensor medium contains non-conductive granulate, such as glass or ceramic material, and a conductive polymer. When the electrode cable is compressed, thereby reducing the distance between the conductors, the density of insulating material increases, thus leading to a change in the resistance between the conductors.

In an additional advantageous embodiment of the sensor according to the invention, the sensor medium is a piezoelectric material, preferably in powder form, and silicone rubber. This results in a piezoelectric-based pressure and heart movement sensor, with no loss of electrode cable flexibility and no hard, brittle piezoelectric elements, with which the piezoelectric voltage can be measured between existing electrode conductors.

In another advantageous embodiment of the sensor according to the invention, the conductors are formed of two electrical conductors, diametrically opposite one another, extending longitudinally inside a flexible hose. This increases the sensor sensitivity.

In an embodiment of the invention employing a bipolar electrode system with an electrode tip connected to a helically wound inner conductor and a coaxial ring connected to a helically wound outer conductor, the sensor medium is arranged between the inner and outer helices and the impedance between the ring and tip is large enough to prevent the formation of an electrical connection between the electrode tip and the ring when the desired electrical quantity is measured between the conductors.

In the case of a bipolar pacemaker electrode system with the conductors coiled in two helices, one inside the other, the impedance between the two helices or between the outer helix and the surroundings, or both impedances, can be used for detecting heart movements. When the impedance between electrode conductor and the surroundings is utilized, the enclosure of the heart stimulator serves as a connection for the surroundings. The capacitance can be used as the measured electrical quantity instead of the impedance.

According to another advantageous embodiment of the sensor of the invention, the conductors of the electrode cable are enclosed in silicone which swells when penetrated by fluid so its dielectric constant changes, leading, in turn, to an increase in the capacitance to be measured. This is an advantageous effect, since it facilitates measurement of the capacitance, and a more reliable sensor is attained.

According to further advantageous embodiments of the sensor of the invention, the measurement device is a measurement oscillator, devised so its frequency changes according to the electrical quantity measured. A difference former is suitably arranged to determine the difference between the frequency dependent on the electrical quantity from the measurement oscillator and a reference frequency supplied by a reference oscillator. A frequency/voltage converter is connected to the output terminal of the differentiator. The converter delivers an output voltage signal, representing the frequency difference, and thus the change in the electrical quantity.

DESCRIPTION OF THE PREFERRED EMBODIMENTS

Figure 1:
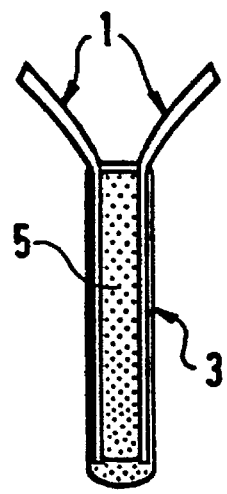
FIG. 1 shows a part of the electrode cable, forming a sensor constructed in accordance with the principles of the present invention, in a bipolar electrode system with two conductors arranged in a silicone rubber flexible tube.

FIG. 1 shows a part of the electrode cable in a bipolar electrode system with two conductors 1 arranged inside a silicone rubber flexible tube 3. The conductors 1 are arranged diametrically opposite to one another at the inner side of the flexible tube 3 and extend in the latter's longitudinal direction of the tube 3. The internal diameter of the flexible tube 3 is typically 2 mm, and the wall thickness is a few tenths of a mm.

The flexible tube 3 is filled with a mixture 5 of carbon granules and silicone rubber which fills the entire flexible tube 3. The carbon granulate content should exceed 40%.

The resistance measured between the conductors 1 changes when the flexible tube 3 is subjected to pressure variations caused by heart movements or variations in blood pressure. When the flexible tube 3 is compressed such that the distance between the conductors 1 decreases, the resistance measured between the conductors 1 drops, because of improved contact between the electrically conductive carbon granules.

Instead of being filled with the above mixture 5 of carbon granules and silicone rubber, the flexible tube 3 can be filled with a mixture 5 of carbon granules and a conductive polymer or a mixture 5 of carbon granules and sodium chloride solution, thereby improving the interconduction.

Improved conduction between the conductors 1 is also achieved if the flexible tube 3 is filled with a mixture 5 of carbon fiber mat and silicone rubber.

The mixture 5 in the flexible tube 3 can alternatively consist of a conductive polymer and non-conductive granulate, such as glass or ceramic material. When the flexible tube 3 is compressed in this instance so the distance between the conductors 1 decreases, the resistance changes between the conductors, since the density of granules of insulating material increases.

The flexible tube 3 can alternatively be filled with a mixture 5 of a piezoresistive powder and silicone rubber or a piezoelectric powder and silicone rubber. In the latter instance, a piezoelectric voltage, which varies with the deformation of the electrode cable, can be measured between the conductors 1.

The piezoelectric powder is made by crushing a piezoelectric ceramic material.

Since the piezoelectric crystals are hard and brittle, a solution as above according to the invention has strength advantages compared to the use of conventional piezoelectric elements. In addition, the electrical quantity of interest is measured between existing electrode conductors with no need for any additional conductors.

Figure 2:
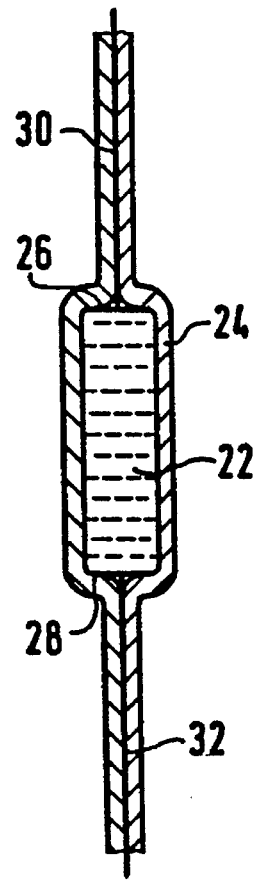
FIG. 2 shows a version of the sensor according to the invention in which the sensor medium constitutes a part of a conductor.

FIG. 2 schematically shows an embodiment in which the sensor medium 22 is enclosed in a cavity inside an elastic tube 24, made from insulating material, between two conductive plates 26 and 28 to which conductors 30 and 32 are connected.

The measurement device is connected to the conductors 30 and 32 to measure e.g., the impedance between the plates 26 and 28.

Alternatively to the above-mentioned types of sensor media, whose electrical properties change when the media are compressed, conductive media, such as electrolytes or conductive gels, can be used as sensor medium 22 in this instance. Here, the sensor medium 22 will constitute a part of the conductors 30 and 32 themselves, and measured changes in impedance, when the part of the flexible tube containing the sensor medium 22 is compressed, are caused by geometric changes in the conductive path. Thus, compression of the flexible tube 24 can result in a reduction in the cross-sectional area of the sensor medium 22 in a given area, thereby narrowing the current path.

Instead of using a fluid or gel sensor medium, enclosed in an outer sleeve, the actual sensor part can be devised in the form of a solid body made from an appropriate sensor medium and arranged between the conductors 30 and 32.

Figure 3:
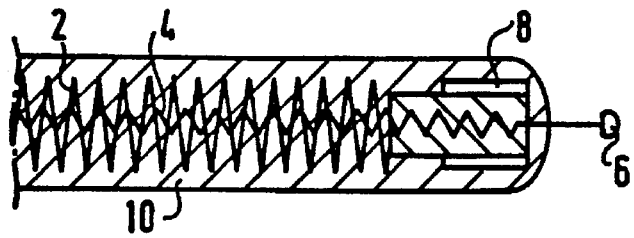
FIG. 3 illustrates a sensor of the invention formed by a portion of bipolar electrode system with two helically coiled conductors, one inside the other.

FIG. 3 shows a bipolar electrode system with two helically coiled conductors 2 and 4, one inside the other. The inner conductor 4 is connected to a tip or stimulation electrode 6, and the outer conductor 2 is connected to an indifferent ring electrode 8. The conductors 2 and 4 are enclosed in an insulation 10. The insulation 10 can consist of a type of silicone which swells when penetrated by fluid, leading to a change in the dielectric constant and an increase in capacitance. The sensor sensitivity also increases as a result.

Figure 4:
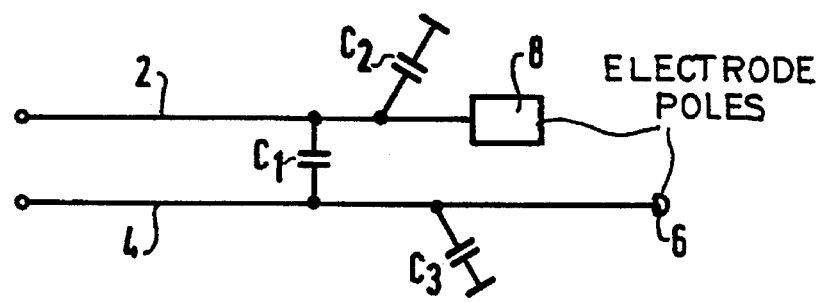
FIG. 4 schematically depicts the capacitance conditions in the electrode system in FIG. 3.

Capacitive couplings exist between the conductors 2 and 4, and between the conductors 2 and 4 and the ambient medium. These capacitive couplings are schematically represented in FIG. 4 by respective capacitances $C_1$, $C_2$, and $C_3$. In the dry condition, the capacitance $C_1$ has been measured to about 100 pF, provided that the electrode poles 6 and 8 are not in contact with one another via electrolyte or body fluid. As shown in FIG. 3, the ring electrode 8 is therefore fully encapsulated against the stimulation electrode 6.

The capacitance $C_1$ between the conductors 2 and 4 changes with the distance between the conductors 2 and 4. Movement and changes in pressure deform the electrode conductors 2 and 4, leading to changes in both the capacitance $C_1$ and the capacitances $C_2$ and $C_3$. In this manner, heart movements will cause changes in the capacitance. Heart movements can thus be sensed by continuous monitoring of the capacitance. In practice, the capacitance $C_1$ between the conductors 2 and 4, or the capacitance $C_2$ between the outer conductor 2 and ambient medium, or both these capacitances, can be used.

Figure 5:
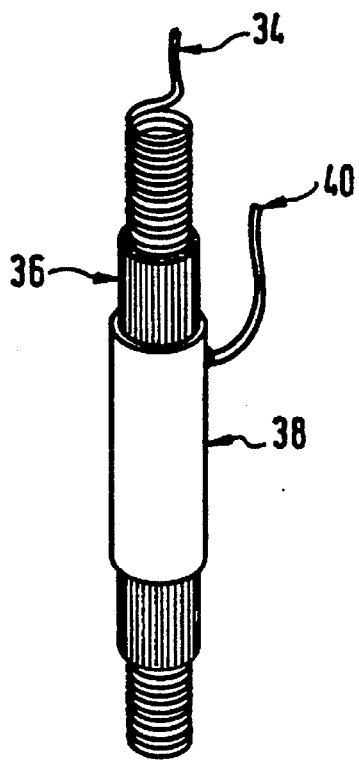
FIG. 5 shows a coaxial version of the sensor according to the invention.

FIG. 5 shows a coaxial version of the invention with an inner conductor 34 in the form of a metal helix, surrounded by a layer 36 of sensor medium. A layer 38 of conductive material, to which a second conductor 40 is connected, is arranged on the exterior of the sensor medium 36. A representative electrical quantity, varying with changes in the pressure on the device, can be measured between the conductors 34 and 40.

Figure 6:
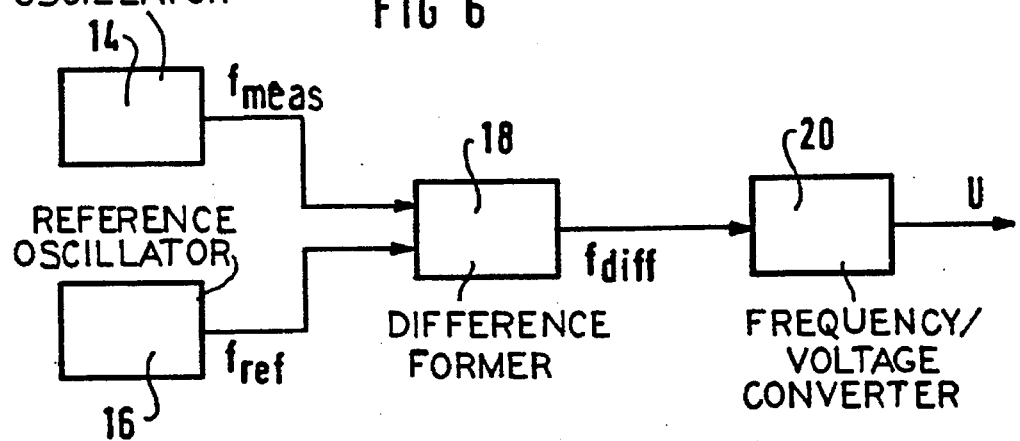
FIG. 6 is a circuit diagram of the measurement device of the invention for converting changes in the measured electrical quantity into an output voltage signal.

FIG. 6 shows a pressure and heart movement sensor according to the invention which contains a measurement device with a measurement oscillator 14 the frequency $f_{meas}$ of which depends on changes in the electrical properties of a sensor medium and/or changes in the measured electrical quantity as a result of geometric changes caused by movement and deformation of the conductors. The measurement device further includes a reference oscillator 16 with a fixed reference frequency $f_{ref}$. The fundamental or center frequency of the measurement oscillator 14 is appropriately chosen equal to the frequency of the reference oscillator 16, and the frequencies $f_{meas}$ and $f_{ref}$ are supplied to a difference former 18 in which the difference between the two frequencies $f_{meas}$ and $f_{ref}$ is established. This differential frequency $f_{diff}$ is supplied to a frequency/voltage converter 20 which converts the differential frequency $f_{diff}$ into a corresponding output voltage signal U, (see FIG. 6).

Figure 7:
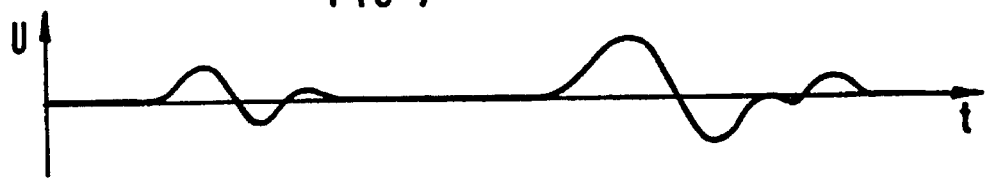
FIG. 7 shows an example of the output signal from the measurement device in FIG. 6.

FIG. 7 shows an example of the output voltage U versus time. A large output voltage U means a large frequency difference $f_{diff}$ which, in turn, corresponds to a large change in the representative electrical quantity caused by e.g., a major change in pressure or heart movement.

Figure 8:
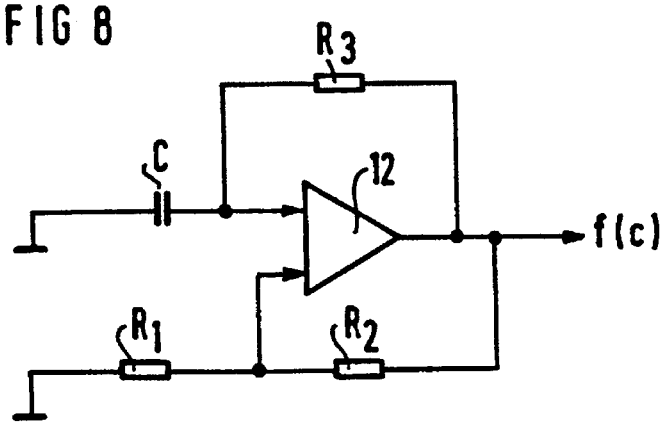
FIG. 8 is a circuit diagram for an oscillator with a capacitance-dependent frequency which can be realized in the measurement device in FIG. 6.

FIG. 8 shows a circuit example of the measurement oscillator 14 of FIG. 6, the frequency f(C) of which is a function of the capacitance C at the input. Thus, the capacitance C is connected to one input of an amplifier 12, the other input of which is connected to a fixed reference value, determined by the resistor $R_1$. The output of amplifier 12 is fed back to its inputs via respective resistors $R_2$ and $R_3$ as shown in FIG. 8.

The oscillator's frequency f then becomes $$f = \frac{1}{2R_3 \cdot C \cdot \ln(1 + 2R_1/R_2)},$$

i.e., the frequency f becomes a function of the capacitance C.

When the amplifier 12 is arranged so that either the capacitance $C_1$ between the conductors 2 and 4 in the bipolar electrode system, or the capacitance $C_2$ between the outer conductor 2 and the ambient electrolyte forms the capacitance C, an oscillator is obtained having an output frequency (C) which is a function of the capacitance $C_1$ or $C_2$ and which changes when the shape of the electrode conductors changes. Heart movements thus can be detected from the output frequency f(C).

The invention has been described herein in the context of a bipolar electrode system. The invention is also applicable, however, to an unipolar electrode system, the measurement oscillator then being controlled by, e.g., the capacitance between the conductor and the ambient electrolyte. The heart stimulator's capsule then forms the connection for the ambient medium.

Although modifications and changes may be suggested by those skilled in the art, it is the intention of the inventors to embody within the patent warranted hereon all changes and modifications as reasonably and properly come within the scope of their contribution to the art.

We claim as our invention:

1. In an implantable heart stimulator including an electrode system having an electrode cable containing at least two electrical conductors leading to electrode poles, the improvement of a pressure and heart movement sensor comprising:

measurement means for measuring an electrical quantity between said electrical conductors varying dependent on pressure applied to said electrode cable.

2. The improvement of claim 1 wherein said measurement means comprises a sensor medium disposed between said conductors, said sensor medium having electrical properties which change when said medium is compressed when subjected to an external pressure, said electrical properties of said medium comprising said electrical quantity varying dependent on pressure applied to said electrode cable.

3. The improvement of claim 1 wherein said measurement means comprises a sensor medium including a portion of one of said conductors, said sensor medium having electrical properties which change when said medium is compressed when subjected to an external pressure, said electrical properties of said medium comprising said electrical quantity varying dependent on pressure applied to said electrode cable, and wherein said measurement means is connected to two spaced points on said one of said conductors on opposite sides of said sensor medium for measuring changes in said electrical quantity arising between said two points when said sensor medium is subjected to external pressure.

4. The improvement of claim 2 wherein said sensor medium comprises an insulating, elastic substance containing granules of conductive material.

5. The improvement of claim 4 wherein said insulating elastic substance comprises silicone rubber.

6. The improvement of claim 4 wherein said granules comprise carbon granules.

7. The improvement of claim 2 wherein said sensor medium comprises a carbon fiber mat contained in silicone rubber.

8. The improvement of claim 2 wherein said sensor medium comprises carbon granules contained in a conductive polymer.

9. The improvement of claim 2 wherein said sensor medium comprises a non-conductive granulate contained in a conductive polymer.

10. The improvement of claim 9 wherein said non-conductive granulate is a material selected from the group consisting of glass and ceramic material.

11. The improvement of claim 2 wherein said sensor medium comprises a piezoresistive substance.

12. The improvement of claim 2 wherein said sensor medium comprises a piezoelectric substance, and wherein said measurement means comprises means for measuring a voltage generated by said piezoelectric substance between said conductors.

13. The improvement of claim 12 wherein said piezoelectric substance comprises piezoelectric powder contained in silicone rubber.

14. The improvement of claim 2 wherein said sensor medium comprises carbon granules in a sodium chloride solution.

15. The improvement of claim 2 wherein said sensor medium comprises an electrolyte.

16. The improvement of claim 2 wherein said sensor medium comprises an electrically conductive gel.

17. The improvement of claim 1 wherein said conductors are movable relative to each other, and wherein said measurement means comprises means for measuring an electrical quantity varying dependent on the relative movement of said conductors.

18. The improvement of claim 1 wherein said conductors are deformable, and wherein said measurement means comprises means for measuring an electrical quantity varying dependent on the deformation of said conductors.

19. The improvement of claim 1 wherein said measurement means comprises a flexible tube in which said conductors are disposed separated from each other, and a sensor medium filling said flexible tube.

20. The improvement of claim 18 wherein said electrical conductors are diametrically oppositely disposed and extend longitudinally along an interior of said flexible tube, and wherein said sensor medium is disposed at least between said electrical conductors.

21. The improvement of claim 1 wherein said electrode system comprises a bipolar electrode system having a helical inner conductor connected to an electrode tip forming one of said electrode poles and a helical outer conductor connected to a co-axial ring forming another of said electrode poles, and wherein said measuring means comprises a sensor medium disposed between said inner and outer conductors, and wherein said ring and tip electrodes have a large impedance therebetween.

22. The improvement of claim 1 wherein said measurement means comprises means for measuring resistance between said conductors.

23. The improvement of claim 1 wherein said measurement means comprises means for measuring capacitance between said conductors.

24. A pressure and heart movement sensor for a heart stimulator comprising:

an electrode system adapted for implantation in an ambient body medium and having an electrode cable containing an outer coiled electrical conductor and an inner coiled electrical conductor disposed inside said outer coiled electrical conductor leading to electrode poles; and measurement means for measuring impedance, which varies as said electrode cable is subjected to pressure, between said outer coiled electrical conductor and said ambient body medium and for generating an output signal corresponding to said impedance.

25. A pressure and heart movement sensor as claimed in claim 24 wherein said measurement means comprises means for measuring resistance.

26. A pressure and heart movement sensor as claimed in claim 24 wherein said measurement means comprises means for measuring capacitance.

27. A pressure and heart movement sensor comprising;

an electrode system adapted for implantation in an ambient body medium and having an electrode cable containing at least one electrical conductor leading to one electrode pole;

measurement means for measuring capacitance, which varies as said electrode cable is subjected to pressure, between said conductor and said ambient body medium and for generating an output signal corresponding to said capacitance; and silicone material surrounding said electrical conductor, said silicone material swelling when penetrated by fluid and having a dielectric constant associated therewith which changes when said silicone material swells.

28. A pressure and heart movement sensor comprising:

an electrode system adapted for implantation in an ambient body medium and having an electrode cable containing at least one electrical conductor leading to one electrode pole; and measurement means for measuring impedance which varies as said electrode cable is subjected to pressure, between said conductor and said ambient body medium and for generating an output signal corresponding to said impedance, said measurement means including a measurement oscillator having a frequency which changes dependent on said impedance.

29. A pressure and heart movement sensor as claimed in claim 28 wherein said measurement means includes a reference oscillator having a fixed reference frequency, and means for forming a difference between said frequency of said measurement oscillator and said reference frequency as said output signal of said measurement means.

30. A pressure and heart movement sensor as claimed in claim 29 wherein said measurement means includes a frequency-to-voltage converter connected to an output of said means for forming a difference for generating a voltage as said output signal of said measurement means.

* * * * *

UNITED STATES PATENT AND TRADEMARK OFFICE
CERTIFICATE OF CORRECTION

PATENT NO. : 5,514,171
DATED : May 7, 1996
INVENTOR(S) : Hoegnelid, et. al.

It is certified that error appears in the above-indentified patent and that said Letters Patent is hereby corrected as shown below:

Title page, item [73], Assignee: should read-- "Siemens Elema AB, Solna, to read -- Pacesetter AB, Solna, Sweden --.

Signed and Sealed this

Eighth Day of April, 1997

Attest:

BRUCE LEHMAN

Attesting Officer

Commissioner of Patents and Trademarks